US005584805A

United States Patent [19]

Sutton

[11] Patent Number: 5,584,805

[45] Date of Patent: Dec. 17, 1996

[54] ANIMAL PILL-DISPENSER GUN

[76] Inventor: Matthew R. Sutton, 5131 Parkwood St., Boise, Id. 83704

[21] Appl. No.: 406,027

[22] Filed: Mar. 17, 1995

[51] Int. Cl.[6] .................................................. A61M 31/00

[52] U.S. Cl. .............................. 604/60; 604/57; 222/326; 222/327; 222/386; 221/270; 221/272; 221/268; 119/51.01

[58] Field of Search .................................... 221/268, 270, 221/272, 152, 185; 604/57, 59, 60, 61; 222/386; 119/51.01, 51.03, 156, 174, 215; 47/57.5

[56] References Cited

U.S. PATENT DOCUMENTS 4,518,384 5/1985 Tarello et al. ............................ 604/61
4,583,934 4/1986 Hata et al. .......................... 222/386 X

*Primary Examiner*—James R. Bidwell
*Assistant Examiner*—Khoi H. Tran
*Attorney, Agent, or Firm*—Ken J. Pedersen; Barbara S. Pedersen

[57] ABSTRACT

Embodiments of a pill-dispensing gun for animals are disclosed, each embodiment having an improved, crack- and break-resistant handle. The handle comprises an outer member or sleeve and a core extending through the interior of the outer member and up into the barrel of the gun. The preferred gun is made from readily-available standard PVC pipe pieces, with the handle sleeve made of two parts joined by an adhesive and then joined to an elbow of the barrel by adhesive. The preferred core is a rigid tube that extends past the discontinuity or joint between the handle and the barrel to give extra strength to the handle and the handle-barrel connection. Preferably, the core is glued into the sleeve and the barrel, and preferably an annular space exists between the handle sleeve and the core to produce a laminated handle.

6 Claims, 3 Drawing Sheets

ANIMAL PILL-DISPENSER GUN

BACKGROUND OF THE INVENTION

1. Field of the Invention

This invention relates generally to apparatus for administering pills to animals, and, more specifically, a plunger-style pill gun for injecting pills and medicine into the throats of cattle.

2. Related Art

Pill-dispensing guns, often called "bolus guns" or "bailing guns", have been designed for pushing a pill into the throat of cattle and other animals to administer medicine, such as antibiotics, antacids, or antiparasitic medicines. Some of these bolus guns are for delivering multi-doses and have a long, hollow barrel and an internal plunger or push-rod. One or more pills are inserted into the barrel with the plunger handle pulled back to open up the barrel interior space. The barrel is then inserted into the throat of the animal until the barrel front end opening is behind the back of the tongue or even deeper in the animal's throat. The plunger is then pushed forward to shoot or deposit the pills in the throat, so that the animal swallows the pills instead of coughing or spitting them out.

While the bolus gun is being used with large animals, great amounts of force are put on the gun. The long barrel is inserted deeply into the throat of the animal while the veterinarian or caretaker holds on to the animal's head or neck and operates the handle end. In addition, the bolus gun is often dropped to the ground or wedged between, for example, the animal and a fence or other animal pen structure. The bolus gun is often used in winter in sub-freezing or sub-zero temperatures, which makes many guns brittle and prone to cracking.

Bolus guns that are made of metal are known to be prone to denting, bending, and breaking. Making a sturdier metal bolus gun results in so much weight that the gun is undesirable.

A multi-dose gun made out of PVC piping, results in a light-weight, economical, and reusable gun. A PVC bolus gun has been made with a short, hollow, PVC pipe handle extending down from the barrel at about a 90° angle to the longitudinal axis of the barrel. A problem with this gun is that the handle often cracks or breaks due to the stresses placed on it.

Therefore, what is still needed is a bolus gun that efficiently dispenses pills to animals, but that is light-weight, sturdy and durable. What is needed is a handle design that stands up to the repeated and extreme stresses of dispensing pills to cattle and other large animals.

SUMMARY OF THE INVENTION

The present invention comprises an apparatus or "bolus gun" for administering pills and other medicines or nutrients to an animal by inserting a rigid delivery tube or barrel into the animal's throat and pushing a pill or pills through the tube into the throat. A plunger member extends through the barrel and is adapted to be withdrawn backwards to make room in the barrel so that pills may be inserted into the barrel and adapted to be pushed forward to push the pills out of the barrel through the barrel mouth or front end opening. Preferably two stops are included on the rod, one for limiting and/or stabilizing the rod movement as it is withdrawn and one for limiting and/or stabilizing the rod movement as it is pushed forward to deliver the pills.

The bolus gun includes a handle comprising an outer handle member or sleeve and a reinforcing core member. The core member preferably extends up into the barrel, past the joint between the barrel and the handle. The preferred handle includes a space between the core member and the interior surface of the handle sleeve for receiving cement to create a laminated handle.

The improved bolus gun handle stands up to repeated and hard use and to cold weather without cracking or breaking. The laminated handle results in a very durable and effective design that endures the stresses placed on it during use with large animals.

DETAILED DESCRIPTION OF THE PREFERRED EMBODIMENT

Figure 1:
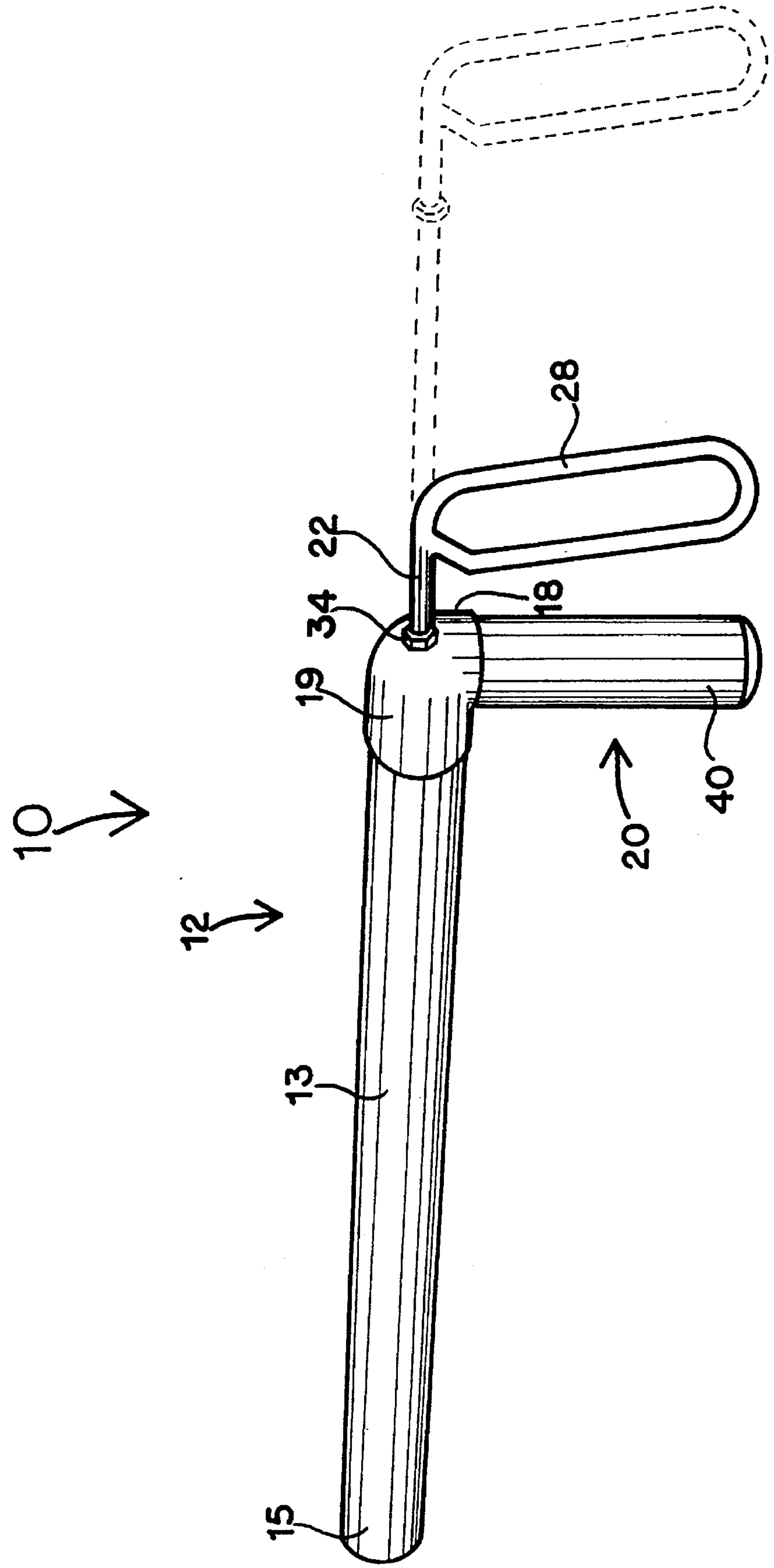
FIG. 1 is an isometric side view of one embodiment of the invention, showing the internal plunger pushed into a forward position to deliver pills, and, in dashed lines, pulled to a withdrawn or backward position to receive pills.
Figure 2:
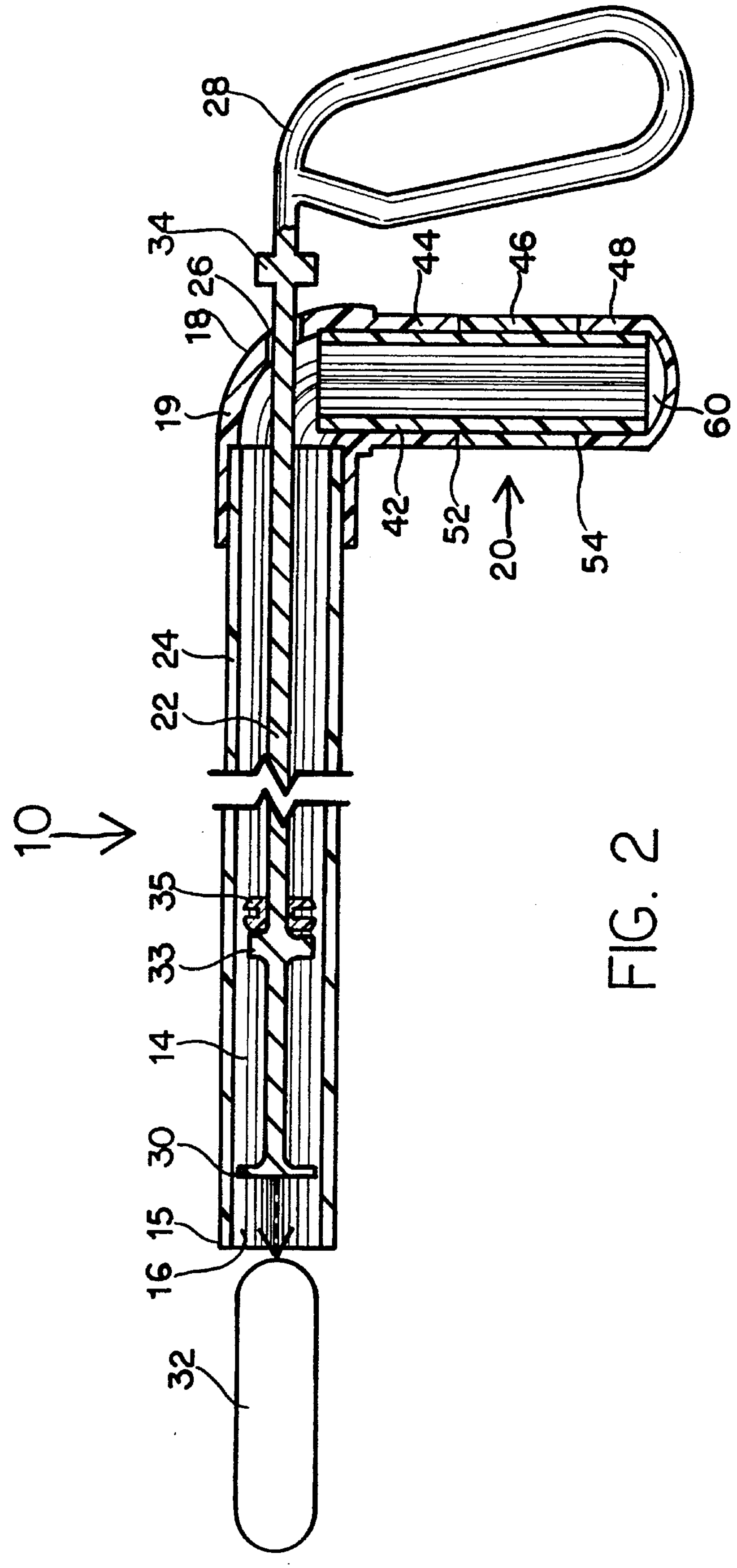
FIG. 2 is a cross-sectional view of the embodiment of FIG. 1 in the forward position.
Figure 3:
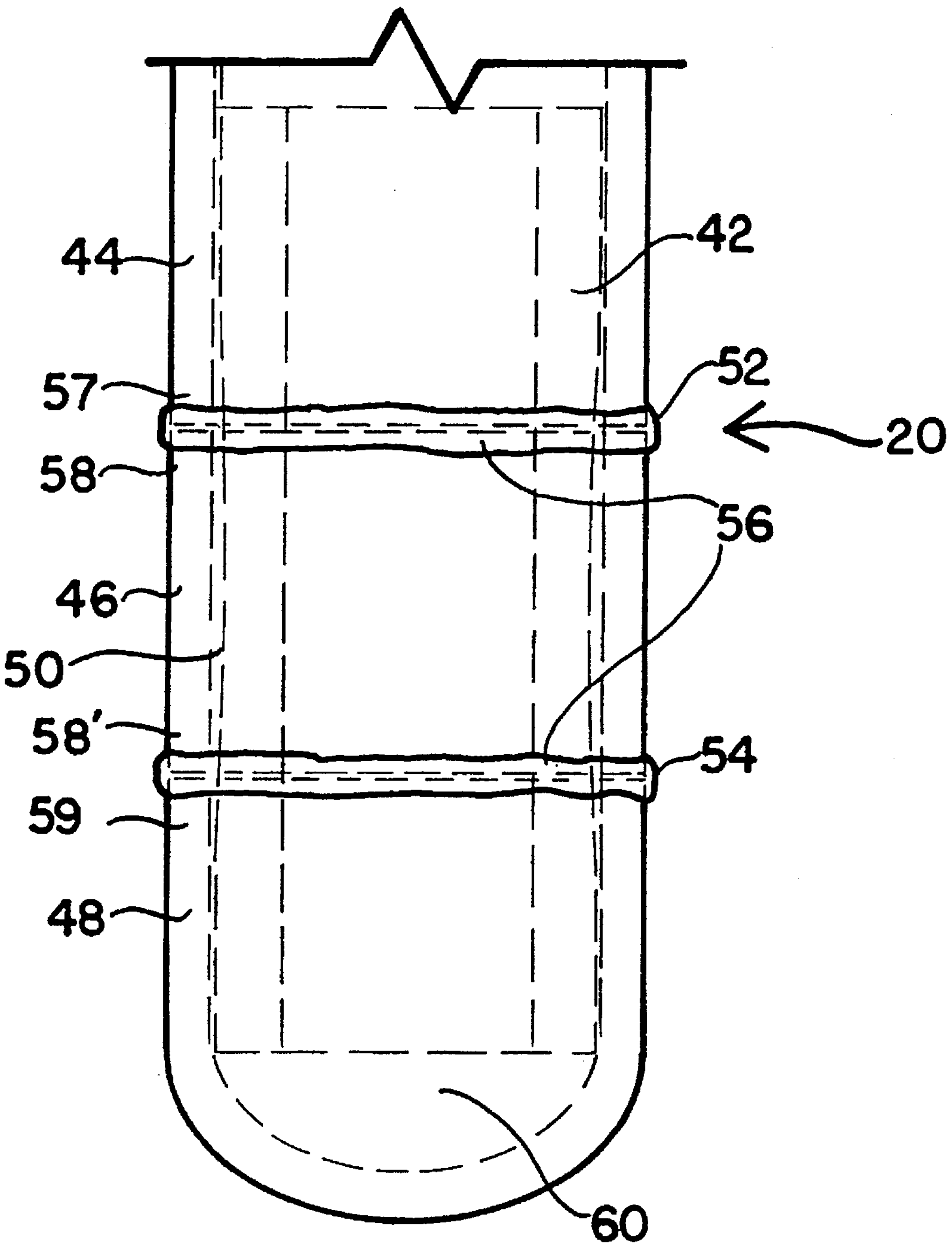
FIG. 3 is a detail, cross-sectional side view of the handle of the embodiment of FIG. 1.

Referring to the FIGS. 1–3, there is shown one, but not the only, embodiment of the invented pill dispenser or "bolus gun" 10. The preferred embodiment 10 may be made from standard pieces and sizes of readily-available PVC piping, which results in the gun being economical to manufacture.

The gun 10 comprises a barrel 12 and a handle 20. The barrel 12 includes the delivery tube 13, which has a hollow interior space 14, and an elbow 19 connected to the delivery tube 13 near the delivery tube or barrel back end 18. The handle 20 is rigidly connected to the barrel 12 at, preferably but not necessarily, about a 90° angle to the delivery tube 13, or, in other words, to the longitudinal axis of the barrel 12.

A plunger rod 22 extends through the interior space 14 and through the barrel wall 24 through an aperture 26 near the back end 18. The rod 22 is generally a straight, elongated member, with a rod handle 28 at its back end. The rod 22 has an enlarged front end 30, which is slightly less in diameter than the inner diameter of the barrel wall 24, for pushing pills through and out of the barrel 12.

The handle 20 and rod handle 28 are preferably generally co-planar and close to each other, for easy manipulation of the gun 10. When the rod handle 28 is pulled backwards, so that most of the rod 22 lies outside of the barrel 12 in a "withdrawn" position, the enlarged front end 30 moves back within the interior space 14, thus, opening up or clearing the way for one or more pills 32 to be inserted into the interior space 14. When the rod handle 28 is pushed to a forward position, the rod front end 30 moves forward inside the barrel, to push the pills 32 to and out of the barrel mouth 16 into the animal's throat, as in a method described above in the Related Art section.

The rod 22 preferably has two stops for limiting the length of the stroke and/or cushioning the stroke. A pull stop 33 is attached to the rod 22 inside the interior space 14 and is positioned along the rod so that it abuts the inside of the barrel wall 24 at or near the barrel back end 18 when the rod 22 is pulled to the desired withdrawn position. A push stop 34 is attached to the rod 22 outside the barrel 12 and is positioned along the rod so that it abuts the outside of the barrel wall 24 around the aperture 26 when the rod 22 is pushed to the desired forward position. The pull stop 33 preferably comprises a nut 33 and one or more cushioning rings 35 that extend around the rod, for serving a cushioning function as well as assisting in the limiting function. The push stop 34 may comprise a nut fixedly attached around the rod, preferably about two inches in front of the rod handle 28, for providing a push limit to prevent the user's hand or fingers from hitting or being pinched between the barrel handle 20 and the rod handle 28.

The handle 20 has an outer handle member, herein called a "sleeve" 40, and a core 42. The handle sleeve 40 preferably, but not necessarily, is generally cylindrical and comprises two members that are connected to the elbow end 44. The two members of the sleeve 40 are: a tube member 46, and a cap member 48. The elbow end 44 and the tube member 46 join at a first joint 52, and the tube member 46 and the cap member 48 join at a second joint 54. At the joints 52 and 54, the elbow end 44 and the two sleeve members 46 and 48 touch or come close together, with preferably the joints 52, 54 comprising cement 56 between and around the ends of the elbow end 44 and two sleeve members 46 and 48. Preferably, the ends 57, 58, 58', 59 are cut or sanded to have flat end surfaces that are parallel and close-fitting when they meet to make butt joints 52, 54.

Thus, the cement 56 connects together the two sleeve members into a rigid sleeve 40 that has a consistent outer diameter for a comfortable grip and a smooth design. The cement 56 also connects together the sleeve 40 and the barrel 12, by connecting the sleeve 40 to the elbow 19.

Preferably, the elbow end 44 and the two sleeve members 46 and 48 are standard pieces of PVC piping. Preferably, the cement 56 at the joints 52, 54 connecting the ends 57, 58, 58', 59 of the elbow end 44 and sleeve members 46, 48 is standard PVC cement, or any adhesive capable of securing the elbow end 44 and two members 46, 48 together with their ends touching or being less than about 1/64 inches apart. Thus, the term "cement" may include any adhesive, such as PVC cement, epoxy, or other binding agents that provides the desired strong connection.

Inside the sleeve 40 is the core 42, which is elongated and extends through an inside space 60 of the two sleeve members 46 and 48 and up into the barrel 12. Preferably, the core 42 extends from cap member 48, through the tube member 46, and into the elbow 19 of the barrel 12 to provide a continuous, reinforcing core that extends past the discontinuity between the handle 20 and the barrel 12, or, in other words, past joint 52.

Preferably, the core 42 is cemented into the sleeve 40 and into the elbow 19. Preferably, an annular space 50 or other gap exists between the exterior surface of the core 42 and the interior surface of the sleeve 40, for receiving cement 56 to create a lamination effect. This lamination creates an extremely sturdy handle 20 and sturdy connection between the handle 20 and the barrel 12.

Preferably, the barrel 12 is 1" inner diameter Schedule 40 PVC (polyvinyl-chloride) piping, and the rod 22 is metal, such as steel or aluminum. The elbow 19 is a PVC elbow, with a 1" end for connection to the PVC delivery tube 13 and a ¾" elbow end 44 for connection to the handle tube member 46. The tube member 46 and cap end 48 are a ¾ inner diameter, schedule 40 PVC piping and cap, respectively, so that the elbow end 44, tube member 46 and cap end 48 all have the same outer diameter. Preferably, the core 42 is¾" outer diameter, schedule 80 PVC pipe.

The outer diameter of the core 42 is approximately the same as the inner diameter of the sleeve 40, making a tight fit between the core 42 and the elbow end 44 and between the core 42 and the cap member 48. The middle region of the core 42 is preferably sanded or tapered slightly to give it a slightly smaller outer diameter than the sleeve 40 inner diameter, to make a slightly looser fit between the core 42 and the tube member 46. This slightly looser fit helps to make assembly easier and provides the annular space 50 extending substantially round the core 42 for receiving cement 56. The resulting, laminated handle 20 has a smooth, easily-held outer surface and is rigid, break-resistant, and crack-resistant.

After assembly, the handle 20 and rod handle 28 are preferably coated in a plastic or rubber cushioning and grip-enhancing material, such as "Plasti-Dip™" or Rubberize-it™", for providing a non-slip grip for the user, for protecting the handle cement 56 and metal rod handle 28 from sterilization solutions, and for insulating the handle from cold weather. In addition, the rod 22 and any other parts of the gun 10 may be painted.

The preferred embodiment includes two joints 52, 54, but the invention also includes embodiments with one or more than two joints. For example, an embodiment may include a sleeve 40 that is a single piece connected at a single joint to the barrel 12. Or, an embodiment may include a sleeve 40 made from more than two sleeve members.

Although the preferred sleeve 40 and core 42 are generally cylindrical, the invention includes embodiments with other of sleeves 40 and cores 42, such as a curved, square, or other shapes.

Alternatively, other designs of core 42 may be used, for example, a plurality of core members that extend through and are cement-laminated inside several inside spaces in the sleeve. Thus, the term "lamination" may include any embodiment with a plurality of rigid material layers extending coaxially with the longitudinal axis of the handle (or generally, but not necessarily exactly, perpendicularly to the barrel) and a layer or layers of cement or other adhesive between the rigid material layers.

In this description and the claims, the term "barrel" refers to the main body of the gun, which in the preferred embodiment, includes the delivery tube 13 and the elbow 19. Thus, in saying that the handle may be connected to the barrel, it need not be attached directly onto the long delivery tube of the barrel, but may be attached to a fitting such as the elbow or another extension or protrusion of the barrel.

Although this invention has been described above with reference to particular means, materials and embodiments, it is to be understood that the invention is not limited to these disclosed particulars, but extends instead to all equivalents within the scope of the following claims.

What is claimed is:

1. A pill gun for injecting pills into a throat of an animal, comprising:

a barrel having an interior space for receiving the pills and an open front end communicating with the interior space, a plunger member received in the barrel interior space and accessible from outside the barrel, the plunger member adapted to move forward through the interior space to push pills out of the barrel through the open front end and adapted to move backward to make room in the barrel interior space for the pills, and a laminated handle connected to the barrel and having a longitudinal axis, the handle comprising:

a plurality of rigid material layers extending parallel to the longitudinal axis of the handle, and adhesive between the rigid material layers.

2. A pill gun as set forth in claim 1, wherein the rigid material layers are substantially cylindrical.

3. A pill gun for injecting pills into a throat of an animal, comprising:

a barrel having an interior space for receiving the pills and an open front end communicating with the interior space, a plunger member received in the barrel interior space and accessible from outside the barrel, the plunger member adapted to move forward through the interior space to push pills out of the barrel through the open front end and adapted to move backward to make room in the barrel interior space for the pills, and a handle connected to the barrel and comprising:

an outer sleeve having an inside space, and a core member received in the inside space of the outer sleeve and extending up into the barrel, wherein a gap is between the outer sleeve and the core member and wherein cement is received in said gap.

4. A pill gun as set forth in claim 3, wherein the gap is substantially annular.

5. A pill gun as set forth in claim 4, wherein the outer sleeve comprises:

a tube member adhesively connected to the barrel, and a cap member adhesively connected to the tube member, and wherein the tube member and the cap member have equal outer diameters.

6. A pill gun for injecting pills into a throat of an animal, comprising:

a barrel having an interior space for receiving the pills and an open front end communicating with the interior space, a plunger member received in the barrel interior space and accessible from outside the barrel, the plunger member adapted to move forward through the interior space to push pills out of the barrel through the open front end and adapted to move backward to make room in the barrel interior space for the pills, and a handle connected to the barrel and consisting of:

an outer sleeve having an inside space, a core member received in the inside space of the outer sleeve and extending up into the barrel, and adhesive between the outer sleeve and the core member.

* * * * *